United States Patent [19]
Canter et al.

[11] Patent Number: 6,159,159
[45] Date of Patent: Dec. 12, 2000

[54] APPARATUS AND METHOD FOR MONITORING OVULATION

[75] Inventors: Joseph M. Canter, Lexington; Yongwu Yang, Belmont; Wanglong Zhou, Reading, all of Mass.; Victor S. Sapirstein, Pound Ridge; Melvin P. Ehrlich, Roslyn Estates, both of N.Y.; James S. Harrison, Ringwood, N.J.; Eugene Katsman, Arlington, Mass.; Omanand Koul, Burlington, Mass.; Michael Y. Lu, Lexington, Mass.; Michael A. Greenwald, Brookline, Mass.

[73] Assignee: SerOptix, Inc., Woburn, Mass.

[21] Appl. No.: 09/224,182

[22] Filed: Dec. 31, 1998

Related U.S. Application Data

[60] Provisional application No. 60/079,558, Mar. 27, 1998.

[51] Int. Cl.[7] .................................................. A61B 10/00
[52] U.S. Cl. .............................. 600/551; 436/65; 436/906
[58] Field of Search ..................................... 600/304, 551; 436/65, 164, 181, 906; 359/379, 385, 800, 804; 422/82.05

[56] References Cited

U.S. PATENT DOCUMENTS

| | | | |
|---|---|---|---|
| 4,815,835 | 3/1989 | Jackson | 600/551 |
| 5,043,888 | 8/1991 | Uriarte | 600/551 |
| 5,267,087 | 11/1993 | Weidemann | 359/801 |
| 5,572,370 | 11/1996 | Cho | 359/801 |
| 5,639,424 | 6/1997 | Rausnitz | 422/61 |
| 5,778,649 | 8/1998 | Kosasky | 600/551 |
| 5,836,890 | 11/1998 | Jackson | 600/551 |
| 5,837,197 | 11/1998 | Porrazzo et al. | 422/61 |

*Primary Examiner*—Cary O'Connor
*Assistant Examiner*—Charles Marmor, II
*Attorney, Agent, or Firm*—Pennie & Edmonds LLP

[57] ABSTRACT

A quantitative process for monitoring female fertility cycle wherein the process involves directing a laser beam, preferably generated by a diode laser, onto an area of a slide containing an air-dried sample of a female body fluid. The diffraction pattern resulting from the sample is detected by a two-dimensional photo diode array and analyzed by a microprocessor. If a ferning pattern exists, such pattern will generate a characteristic structure in the diffraction pattern which is then detected by the photo diode array. If no ferning occurs, the corresponding diffraction pattern will be structureless. The microprocessor is programmed with an algorithm to produce a quantitative index of ferning indicating quantitatively the ferning level. Preferably, a plurality of spots on the sample are measured to determine the ferning level at each spot, and the microprocessor then makes a final determination as to final ferning level on the basis of the test results of all of the spots. This significantly increases the reliability of the final test result, since a defect at one test spot or anomaly of one test result will not be fatal to the final result.

14 Claims, 12 Drawing Sheets

APPARATUS AND METHOD FOR MONITORING OVULATION

This application claims the benefit of U.S. Provisional Application No. 60/079,558, filed Mar. 27, 1998.

FIELD OF THE INVENTION

The present invention relates to monitoring the female fertility cycle and more particularly, to a quantitative and optical-based means to determine the degree of ferning and to evaluate the female ovulation status on the basis of the degree of ferning.

BACKGROUND OF THE INVENTION

In a 1995 article in the American Journal of Public Health, Philip Lee and Felicia Stewart from the US Department of Health and Human Services stated that more than half of all pregnancies in the US are unintended and failing to prevent them is not only medically costly, but also personally and socially costly as well. The use of available contraceptive methods, whether natural or artificial, can thus be extremely cost effective as compared with using no contraception.

However, a number of problems a reassociated with available contraceptive methods. Artificial contraceptive methods, such as oral contraceptives, have health risks associated with long term use and are not approved for use by some religious groups. In the case of barrier methods, there are also problems for those who are allergic to latex rubber.

Natural family planning, on the other hand, is recommended by some religious groups. With proper training and commitment, it can be an effective contraceptive method. Moreover, it is non-invasive and involves no chemicals. A number of natural methods have been used to monitor ovulation, including basal temperature tracking, calendar tracking, and luteinizing hormone urine test.

However, these natural methods of family planning are beset with a number of disadvantages. In the case of basal temperature, measurement needs to be performed early in the morning and demands continual monitoring, which renders the test very in convenient.

Moreover, while it is considered the most reliable simple test, it does not provide a forewarning of ovulation. Calendar tracking is also tedious, time consuming, and provides no indicator of actual ovulation. Luteinizing hormone urine test is messy, difficult to administer, inconvenient, and can be expensive.

Currently available natural methods of family planning are made more difficult by the variability of one female's fertility cycle to another. In addition, an individual female's own fertility cycle is subject to erratic changes due to various internal and external factors, such as psychological stress, drugs, ovarian cyst, and sexually transmitted diseases. The currently available tests for fertility have not substantially improved reliability because those tests are qualitative and are thus themselves subject to the same variability that affect fertility cycle. As it has been widely accepted that a woman can conceive from an act of intercourse for a maximum of only about seven days of her menstrual cycle, the reliability of natural family planning thus depends on identifying this fertility time window without ambiguity.

One of the tests that have been used to monitor fertility cycle is the ferning test. Ferning, a widely studied phenomenon, is a physical state assumed by dried saliva during the period of ovulation. The physical basis of ferning is not known, but it does roughly correlate with increases in the chloride content of the saliva. Thus, changes in ionic strength and/or the content of sodium or potassium in the saliva appear to be factors; possible changes in the molecular species of mucopolysaccharides cannot be ruled out. Ferning can be viewed with a low magnification lens, but this method is not quantitative, since some degree of ferning can be observed four to six days prior to ovulation. Consequently, this method of detection can be misleading as a gauge for ovulation.

U.S. Pat. No. 4,815,835 to Corona and U.S. Pat. No. 5,572,370 to Cho disclose a qualitative, optical-based ferning tests comprising a light source and lenses to determine female fertility status using the subject's saliva. In an article in Advances in Contraception (volume 9, 1993, pages 335–340) Barbato et al. disclose another qualitative ferning test using a pocket microscope and a slide for the saliva samples. All of these tests are based solely on qualitative evaluation of the extent of ferning formation in saliva samples, and are thus subject to inaccuracies and uncertainties due to erratic variations in symptoms associated with female fertility. It is therefore desirable to quantitatively monitor female fertility cycle on the basis of ferning. And it is also desirable to quantitatively determine the degree of ferning in a female and correlate such ferning degree to the ovulation status of the female.

SUMMARY OF THE INVENTION

The present invention offers a new approach to ovulation monitoring by quantitatively determining the degree of ferning on the basis of diffraction of light by the crystallized saliva of a female. In contradistinction to conventional methods which are all qualitative, the present invention provides more accurate marks and accurately predicts ovulation. More specifically, according to the present invention, the degree of ferning is determined as follows: First, a fluid sample, such as saliva, is collected from the female as a sample. The sample, after dried, is then subject to a laser light directed onto the sample. The light scattered from the sample is then measured to obtain an intensity profile representative of the degree of ferning. To determine the fertility cycle of the female, the degree of ferning is correlated with the ovulation status of the female.

In a preferred embodiment, a drop of saliva from a female is placed on a glass slide. After air drying, the slide is inserted into an ovulation monitoring device of the present invention for automatic reading. A spot of light from a small diode laser is then projected onto the dried saliva and the diffracted light emanating from it is detected by a two-dimensional photo diode array and analyzed by a microprocessor.

If a ferning pattern exists in the area illuminated by the beam, the two-dimensional structure of the ferning pattern gives rise to a characteristic structure in the diffraction pattern which is then detected by the photo diode array. If there is no ferning, the corresponding diffraction pattern will be structureless. The microprocessor is programmed with an algorithm to produce a quantitative index of ferning level.

In the preferred embodiment, the microprocessor will control the device to take measurements of a predetermined number of spots on a single sample, and then make a determination as to the final ferning degree of the sample on the basis of the test results of all of the spots. This multiple spot testing significantly increases the reliability of the final test results, since a defect at one test spot or anomaly of one test result will not be fatal to the final test result.

BRIEF DESCRIPTION OF THE DRAWINGS

These and other features, objects, and advantages of the present invention will become more apparent from the following detailed description in conjunction with the appended drawings in which.

DETAILED DESCRIPTION OF THE INVENTION

Figure 1:
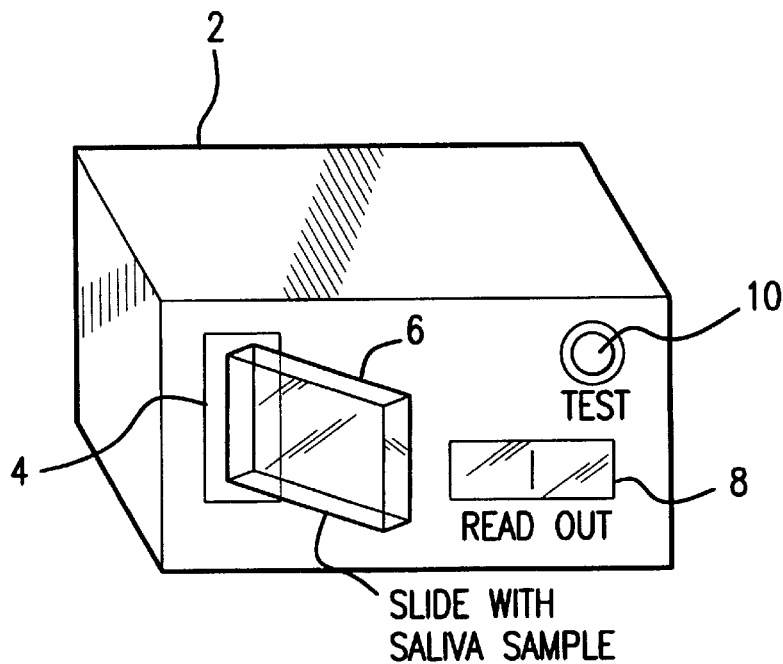
FIG. 1 illustrates a perspective view of a fertility cycle monitor of the present invention for consumer use.

FIG. 1 depicts a perspective view of a fertility cycle monitor 2 of the present invention for consumer use. Illustratively, fertility monitor 2 is portable-sized and has a open slot 4 for receiving a glass slide 6 having thereon an air-dried saliva sample to be tested by the monitor. Preferably, monitor 2 is turned on by the action of inserting sample slide 6 into slot 4, and there is no other on/off switch for this device. A light emitting diode 10 is used to indicate the on-and-off status of the monitor. The monitor includes a liquid crystal display 8 for providing test results and other data, such as time and date, to the user. Inside monitor 2 are an optical system for ferning measurement, a microprocessor for controlling the operation of the system and data collection and data processing, a data storage device for storing fertility cycle information, and other components, which will be described in detail.

Figure 2:
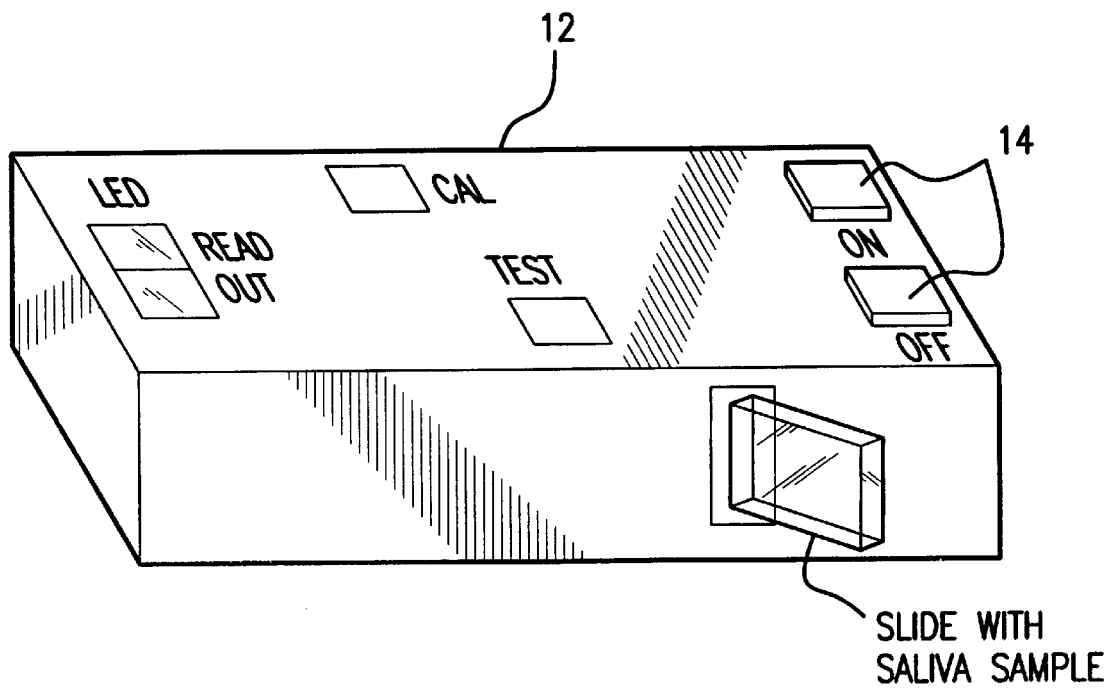
FIG. 2 illustrates a perspective view of a fertility cycle monitor of the present invention for professional use.

FIG. 2 illustrates a perspective view of another fertility cycle monitor 12 of the present invention for professional use. Preferably, as compared with the consumer model in FIG. 1, this professional model is larger in size and has more data storage capacity. Separate on/off switches 14 are provided. The professional model further includes a data interface (not shown) in the back of the system for connecting to a computer. The professional model is more suitable for use when the fertility cycles of a large number of females are to be monitored, such as in a dairy farm. The professional model offers the advantage that it can be connected to a computer for data storage or processing.

Figure 3:
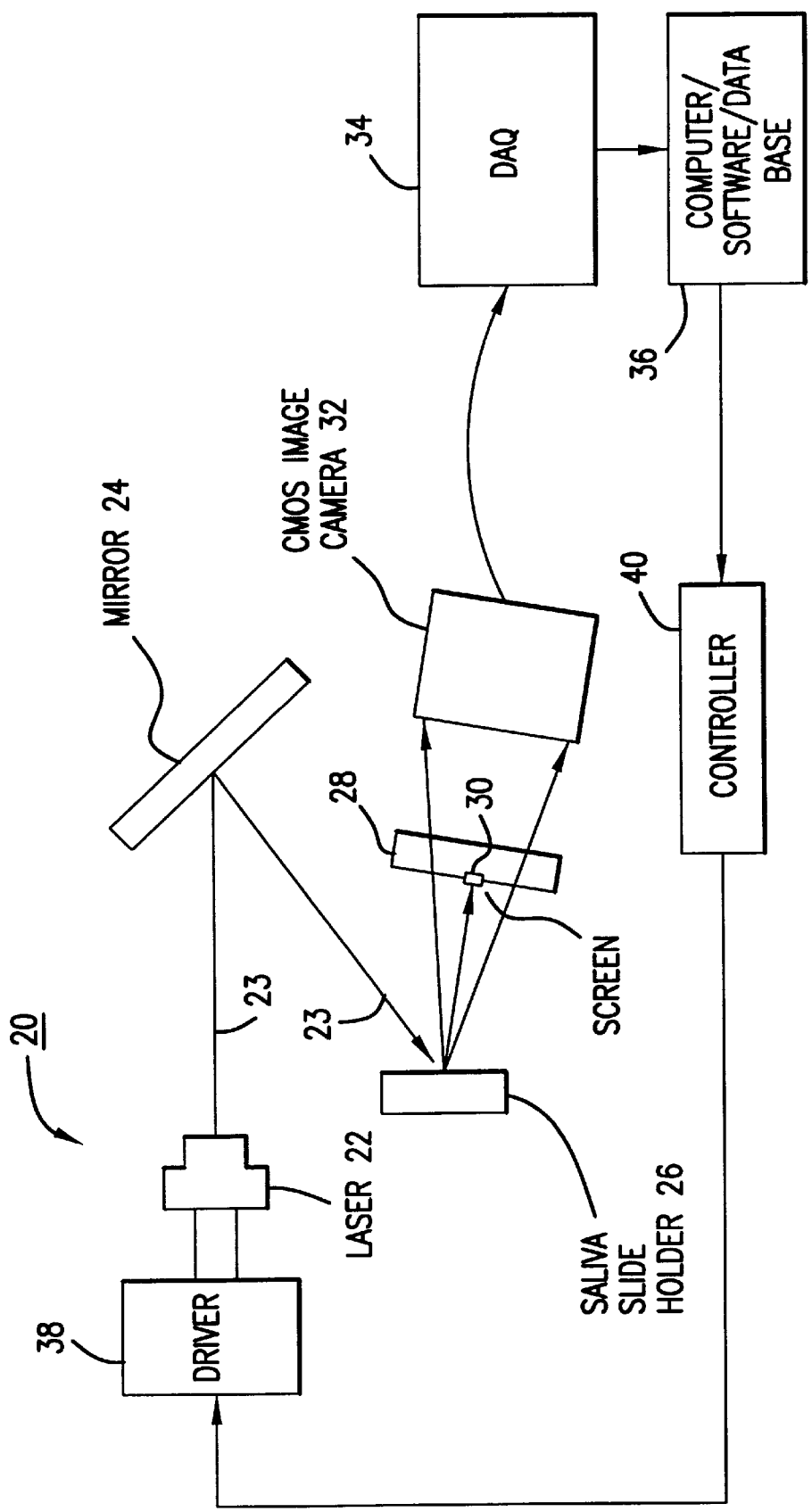
FIG. 3 illustrates a schematic block diagram of a preferred embodiment of the invention.

FIG. 3 illustrates a schematic block diagram of a preferred embodiment of a fertility cycle monitor 20 of the present invention. Fertility cycle monitor 20 includes a 1 milliwatt diode laser 22 which, when turned on, produces a laser beam 23 of 0.25 millimeter in diameter at a wavelength of 635 nanometer. It should be understood, however, that a laser beam of a different beam size can also be used in the invention, and the present invention is not limited to a particular size of the laser beam. Laser beam 23 is projected by a reflective mirror 24 onto a sample glass slide 26 mounted on a two-dimensional movable stage (not shown). The wavelength and power of the diode laser are not critical for the intended operation; 635 nm and 1 mW are presently chosen for convenience. The two-dimensional movable stage is capable of moving up to one centimeter relative and orthogonal to the beam to allow for multiple sampling locations on the slide.

The reflected, scattered and diffracted components of the beam from the saliva sample are projected on a ground glass screen 28. The focal point of the diode laser is on this screen. An opaque dot 30 on the ground glass blocks the specular reflection of the beam. Located behind ground glass 28 is a miniature "chip" camera 32 that digitizes the image utilizing a two-dimensional CMOS photo diode array. The digitized image is then transferred from camera 32 to a data acquisition device 34 before being provided to a microprocessor/computer system 36 and analyzed. Preferably, the microprocessor can be programmed to accept up to 32 images or more from each sample. The fertility cycle monitor further includes a driver circuit 38 for providing an appropriate bias to laser diode 22, and a controller 40 for controlling driver circuit 38 and the movable stage. Controller 40 is controlled by computer 36. It would be apparent to one of skilled in the art that a different type of camera, such as a charge-coupled-device ("CCD") type of camera, can be used in place of the CMOS photo diode array, and the present invention is not limited to a particular type of camera.

Figure 4:
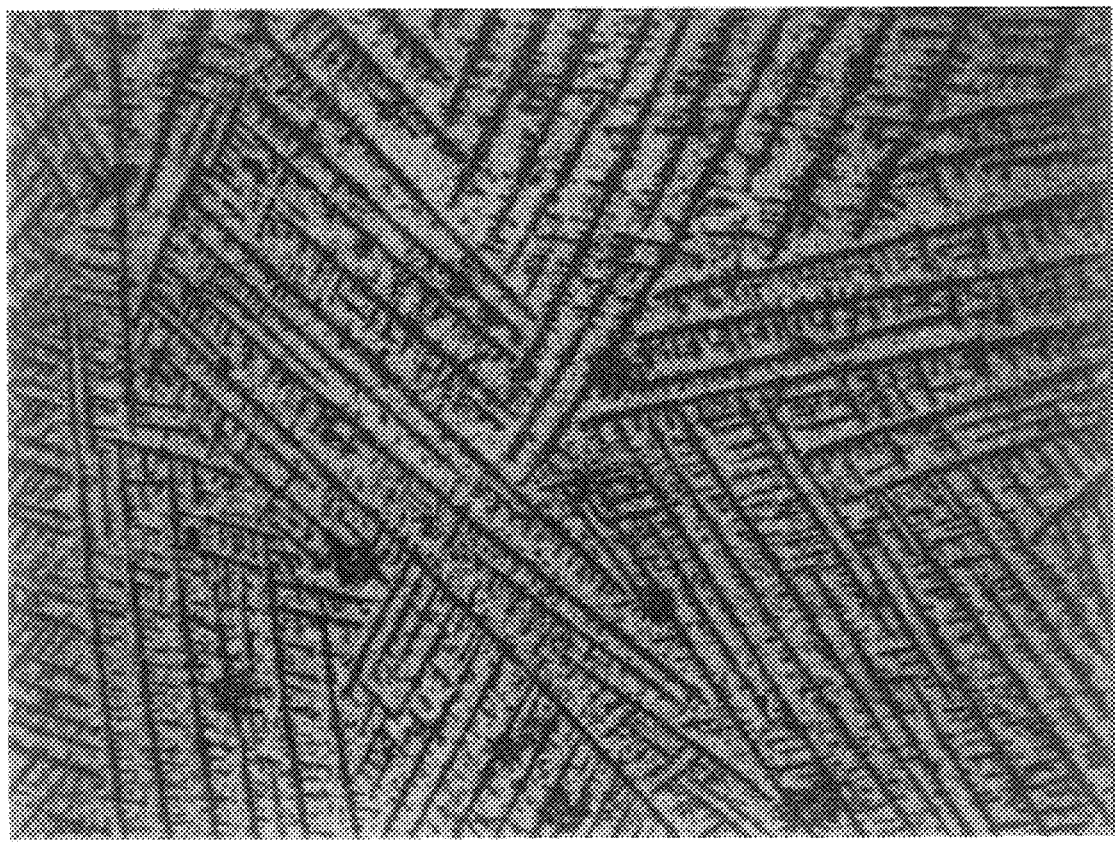
FIG. 4 is a photograph of a dried saliva sample from a female showing a ferning pattern.
Figure 5:
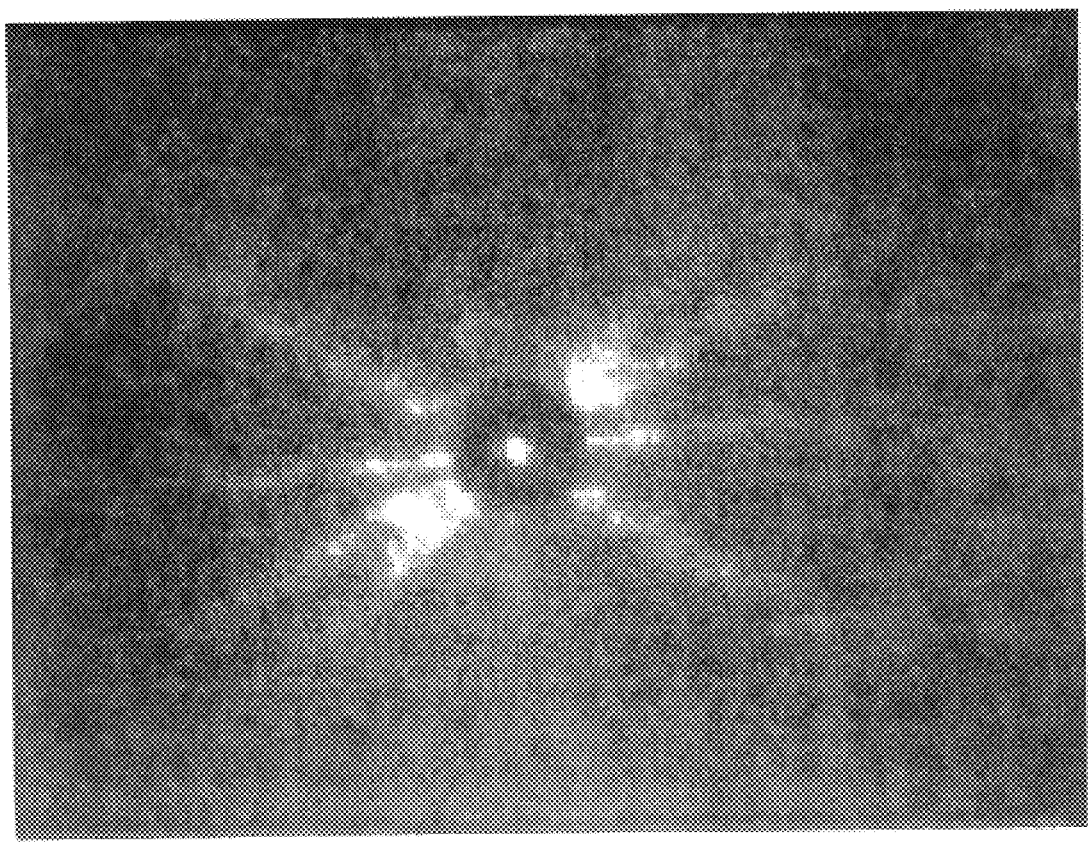
FIG. 5 illustrates an optical diffraction image of a female fernig sample.
Figure 6:
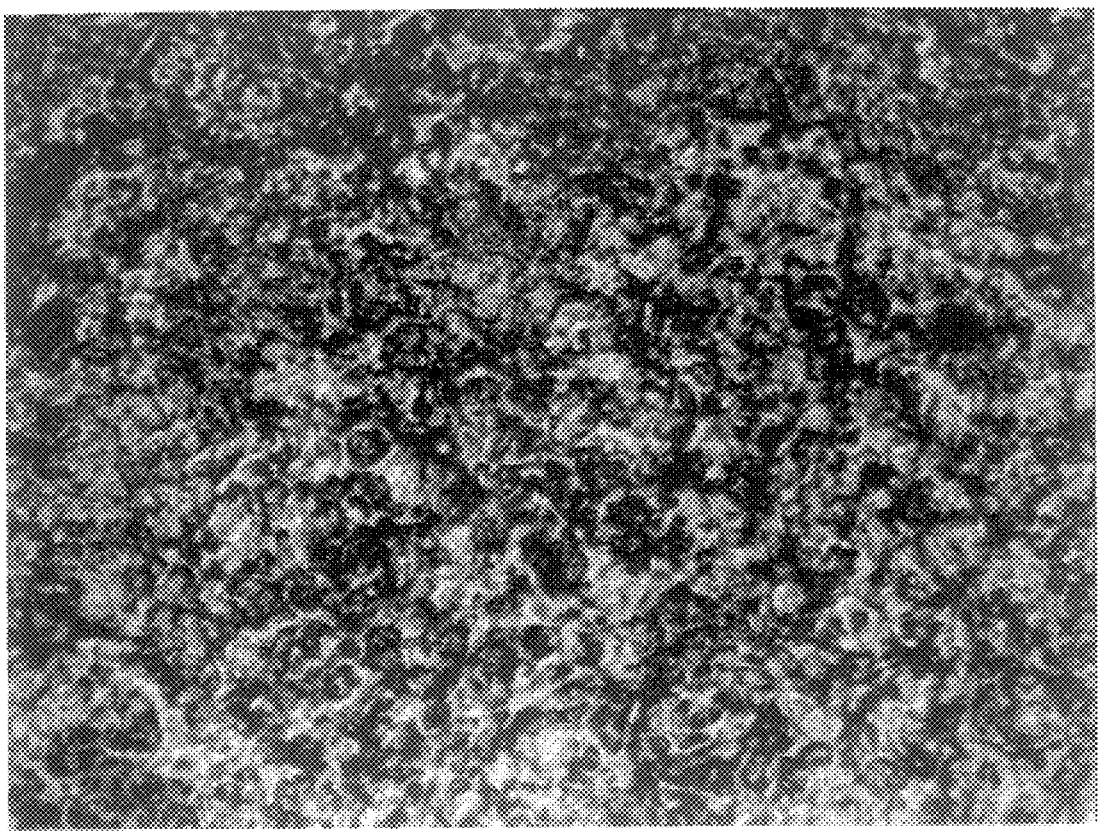
FIG. 6 is a photograph of a dried saliva of a female showing no ferning.
Figure 7:
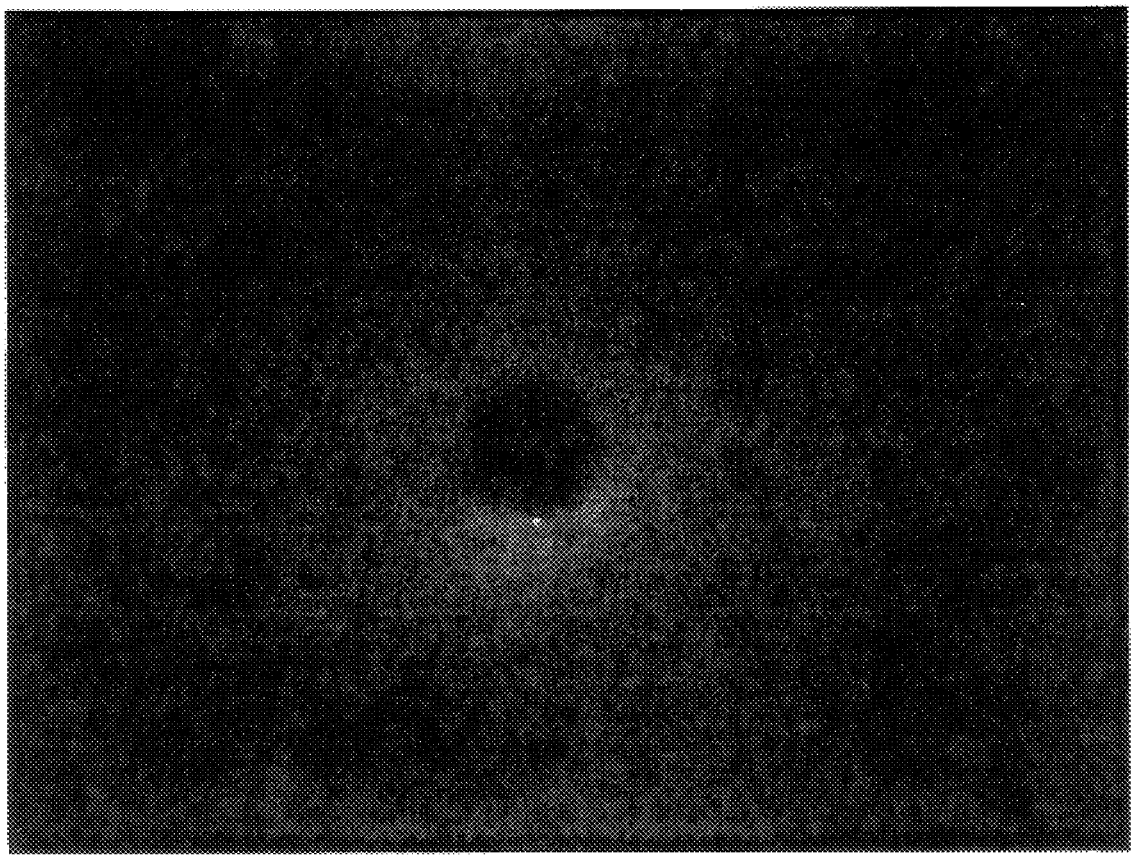
FIG. 7 illustrates a diffraction image of a non-ferning sample.

If there is a ferning pattern (as photographed in FIG. 4) in the area on the sample slide illuminated by the beam, this regular ferning structure in turn gives rise to a characteristic diffraction pattern shown in FIG. 5. If the saliva sample contains no ferning pattern (as shown in FIG. 6), the diffraction pattern is essentially structureless, as shown in FIG. 7. By setting a lower limit of the ferning index defined below, the number of ferning images captures is determined and used as a parameter to calculate a total ferning index for each sample.

Figure 8A:
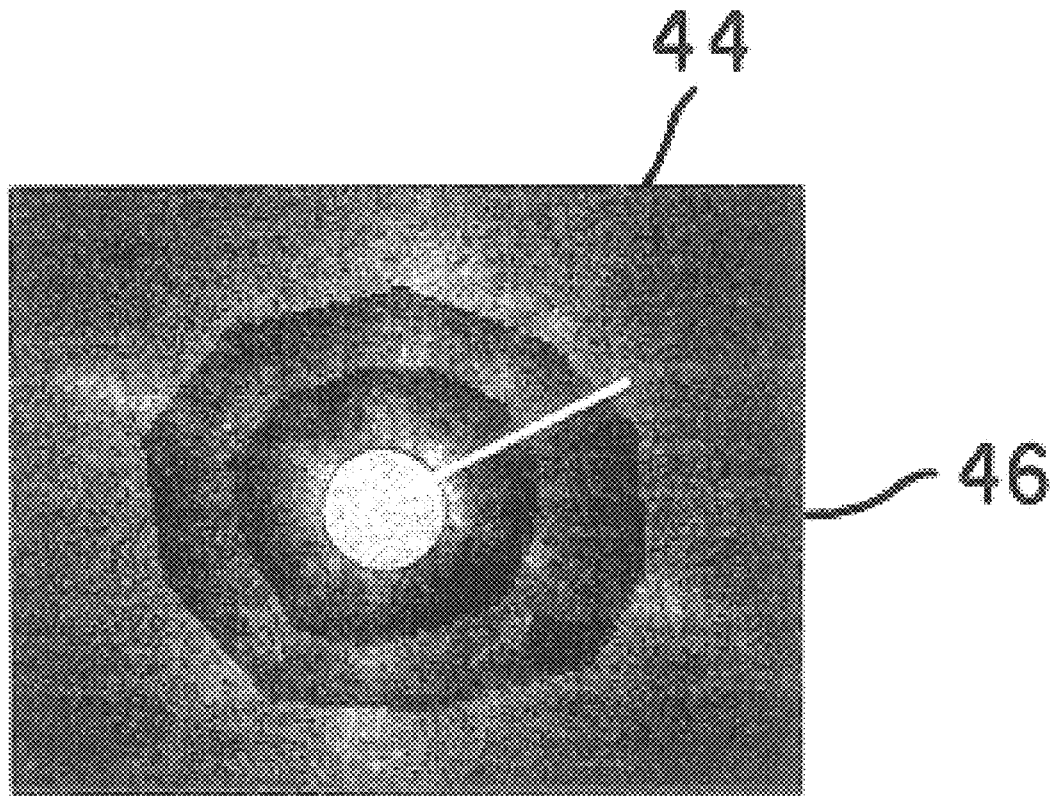
FIGS. 8A–C illustrate ferning image data collection and analysis.
Figure 8B:
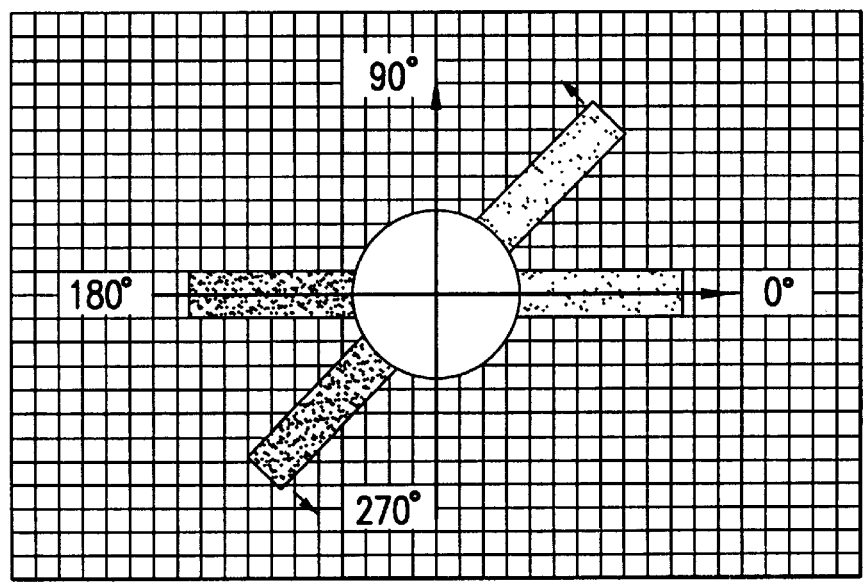
Figure 8C:
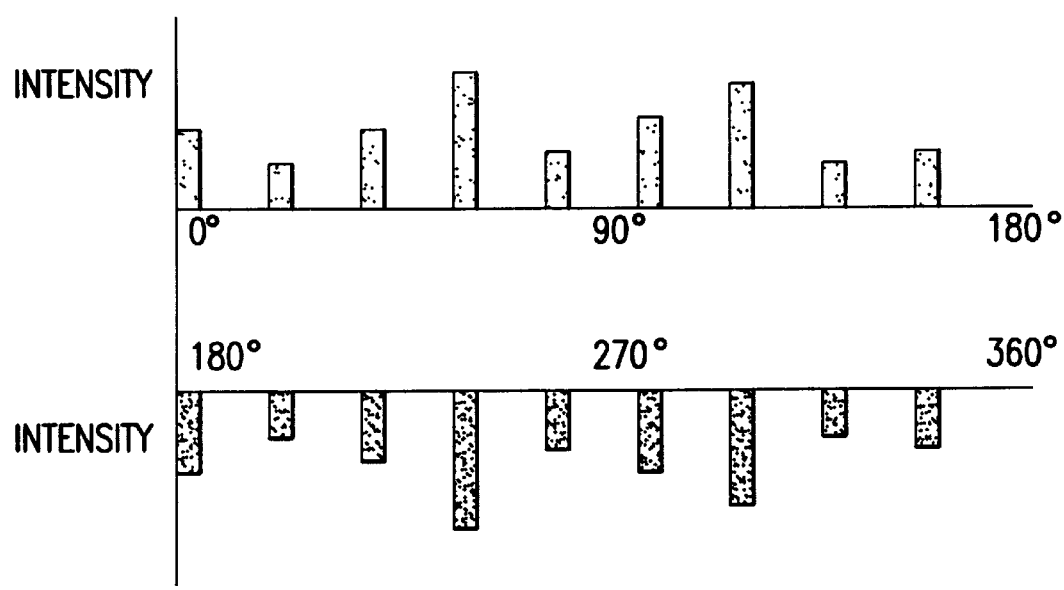

Referring to FIGS. 8A–8C, quantization of the ferning-associated diffraction pattern is performed by analyzing the digitized image. The analysis is performed by sweeping through the image both from 0–180° and 180–360° at 2 degree increments pivoted at the center of the image. Each pixel in a 360 degree array is assigned a grey scale value ranging from 0 to 256. The digital rendering of the diffraction pattern is "masked" by two concentric arcs 44 and 46, as illustrated in FIG. 8A. Only the area between the two arcs will be quantitated.

Figure 9:
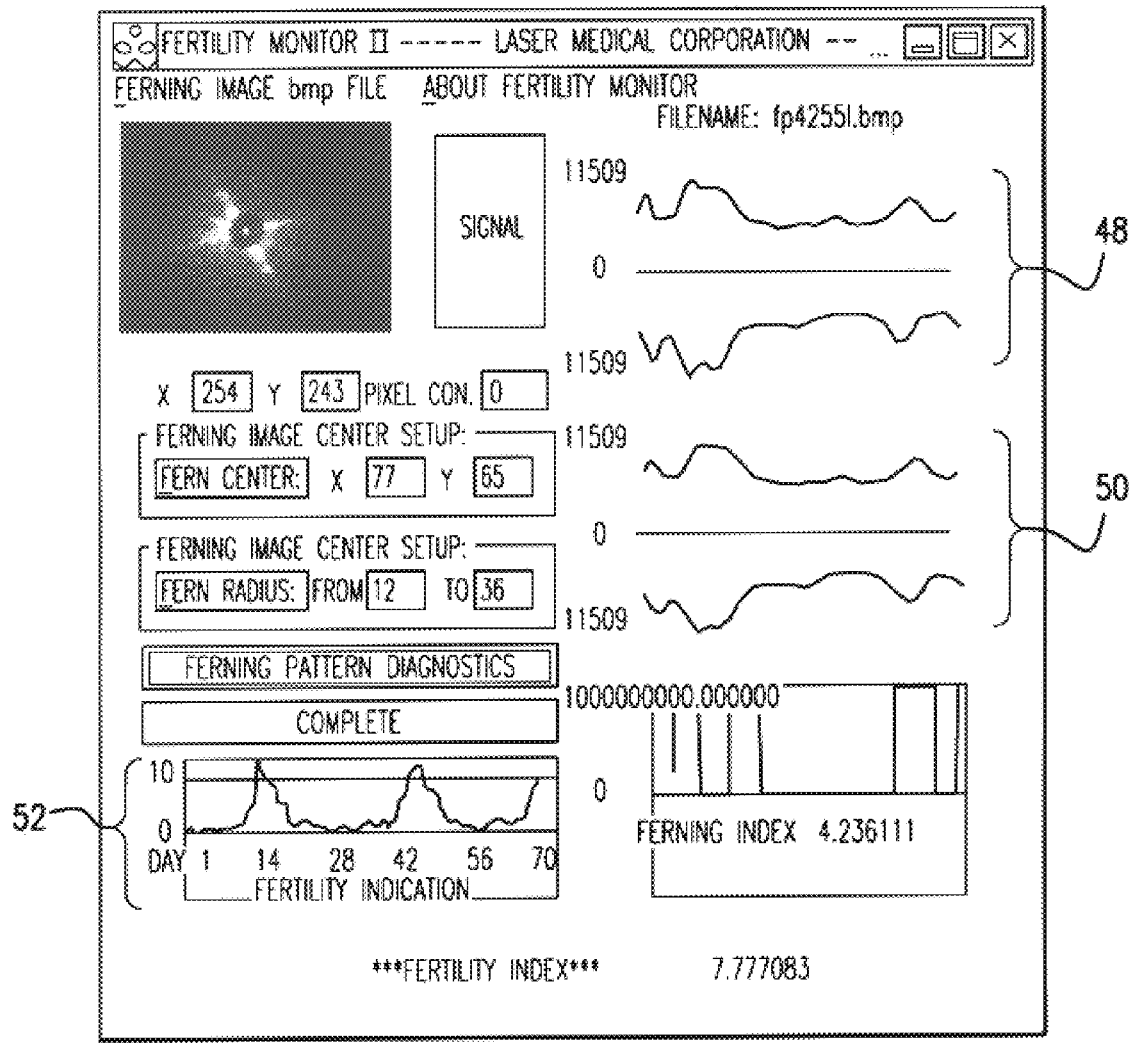
FIG. 9 illustrates a computer display of ferning data.

Referring to FIG. 8C, after performing the image analysis, an intensity profile is constructed which represents the sum of all grey scale values of the pixels within the arcs at that degree increment. Referring to FIG. 9, a linear plot 48 of amplitude is obtained from the diffraction pattern illustrated in FIG. 5. The amplitude plot above the zero line represents, in this display, data points obtained from the 0–180° sweep while that below the zero line represents data points from the 180–360° sweep. In FIG. 9, another liner plot 50 represents the same data but smoothed by a computer signal processing program.

In accordance with the present invention, parameters are provided for use in calculating a ferning index. The parameters are as follows:

Parameter P—This describes the number of peaks which are symmetrically present above and below the zero line. Because of the nature of this parameter, noise and artifact are precluded by this parameter. This parameter measures the number of coherent directions in the ferning (see, e.g., FIG. 5).

Parameter Am—The total amplitude (peak height) of all symmetrical peaks relative to baseline (i.e., the zero line in the linear plot).

Figure 10:
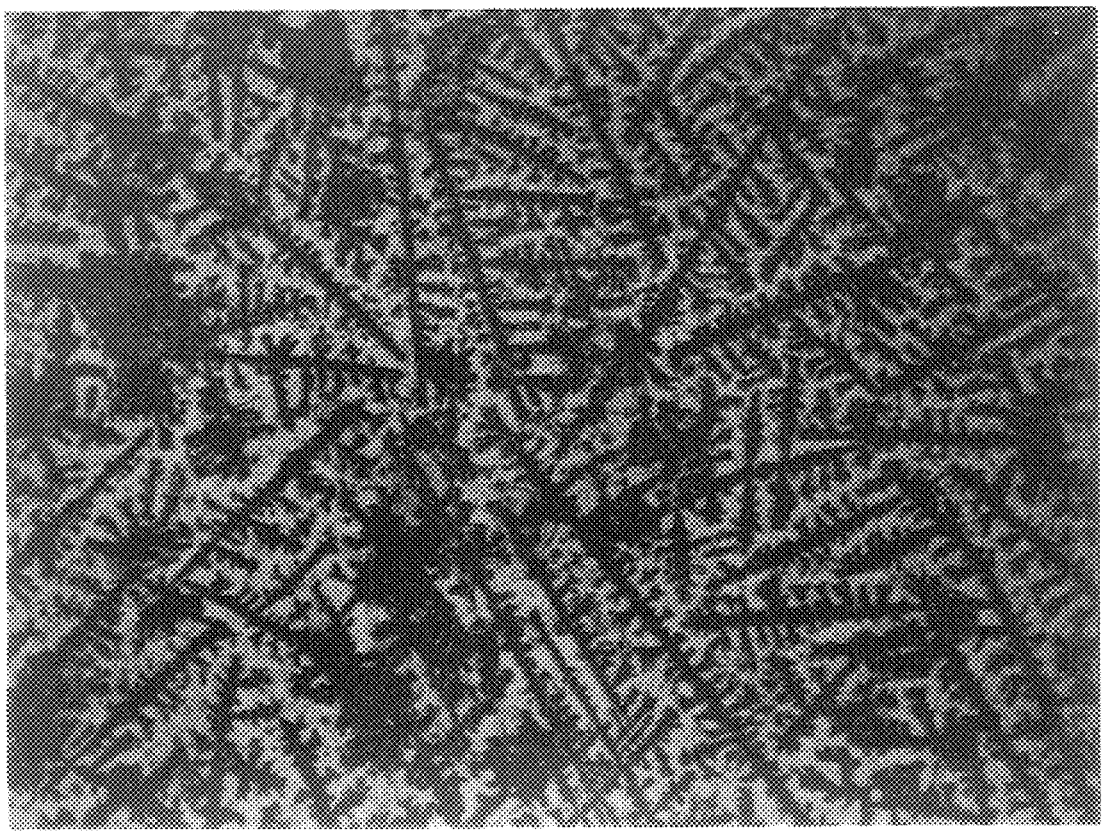
FIG. 10 is a photograph of a dried saliva sample of another female showing ferning.

Parameter Ar—The average area under the curves. This measures the broadness of the peaks and therefore the broadness of the diffraction lines. The importance of this parameter is that it measures the structural complexity of the observed ferning pattern. For example, FIG. 10 is a photograph of a ferning pattern of another sample, which is different from the ferning pattern shown in FIG. 8. The resultant Ar for the two ferning patterns would be different.

In accordance with the present invention, the above parameters are used to compute a local ferning index (i.e., a ferning index corresponds to a single location on the sample from which the data for computing this local index are collected). A local ferning index, IF, may be expressed as a function of the above described parameters IF=f(P, Am, Ar). A minimum (or maximum) value of local ferning index may be selected to allow one to designate these ferning images having local ferning index values less than (or greater than) such minimum (or maximum) value as "true" ferning and the other ferning images as "false" ferning.

In accordance with the present invention, a plurality of locations on a saliva sample are tested and data relating to each of ferning images from these locations are collected using the above-described process. As will be described in detail below, these data from multiple locations will be used to quantitatively evaluate the level or degree of ferning of a ferning pattern. By measuring a plurality of locations of a ferning sample and evaluating data relating to these locations, a more reliable result on the ferning sample is obtained. False test result due to defects of the sample (e.g., a piece of dirt on the dried saliva or a defect spot on the glass slide) or anomaly is significantly reduced.

Referring to FIG. 1, in a preferred embodiment, testing of multiple locations on a sample is provided by moving the sample slide using the movable two dimensional stage (not shown) controlled by controller 40 and computer 36. After a location on the sample slide is tested and data relating to the location are collected, computer 36 is programmed to send instructions to controller 40 to move the sample slide to expose a different location on the sample slide to the laser beam for testing. Preferably, more than eight spots on a sample are tested. In the preferred embodiment, the entire process of testing, moving the slide to test multiple locations, and data collection, storage and analysis are done automatically by or under the control of computer 36 in a short time. It will be apparent to one of skill in the art that alternative methods of projecting the laser beam onto a different location of the sample may be used in the present invention, such as by properly moving mirror 24, screen 28 and camera 32.

In accordance with the present invention, another parameter, the total number of ferning images, TF, is provided. This parameter represents the number of "true" ferning images among the images taken for analysis and determined, for example, according to the above-described process. Using all of the above parameters, i.e., P, AM, Ar, TF, a Global Ferning Index, GFI, is provided, which is described by the analytic function GFI=f(P, Am, Ar, TF).

GFI is then used to determined the degree of fertility of the female whose saliva sample has been collected and tested. Preferably, results for each measurement are stored in a non-volatile RAM in the computer to obtain a historical database for predicting, as well as marking, the day of ovulation as shown in a diagram 52 in FIG. 9.

Figure 11:
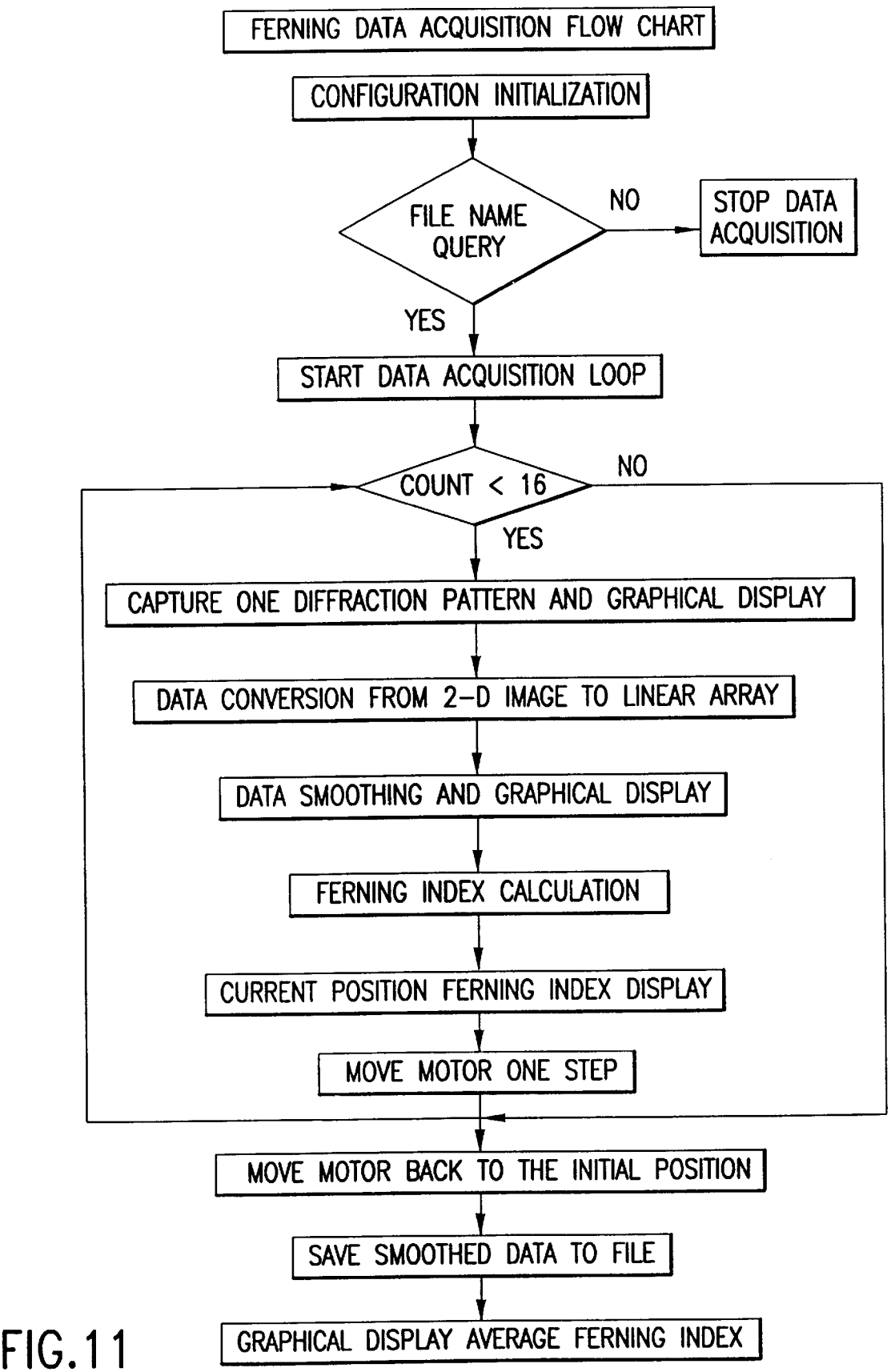
FIG. 11 is a flow chart describing a fernig data acquisition process.
Figure 12:
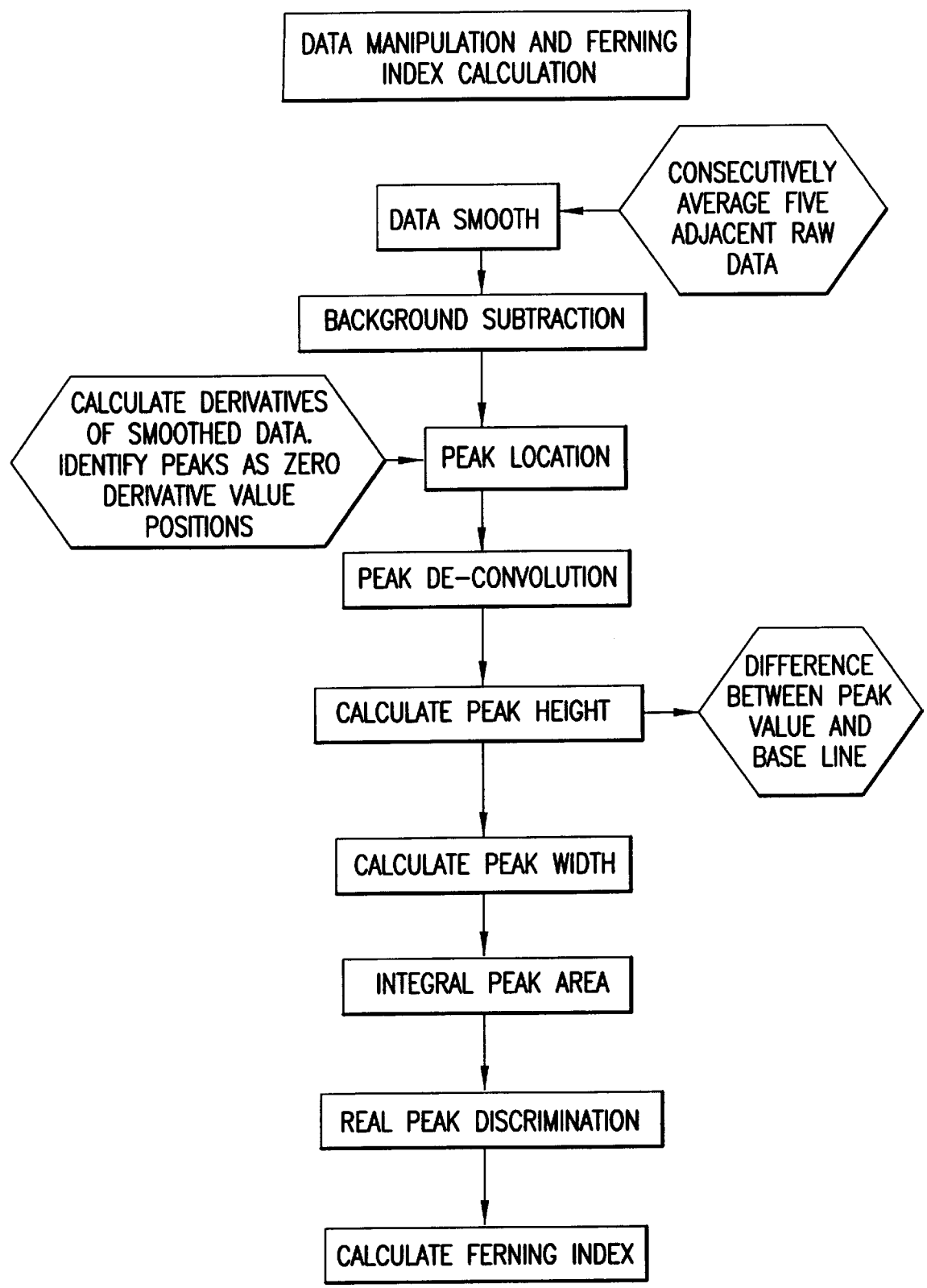
FIG. 12 is a flow chart describing a ferning data analysis process.

FIGS. 11 and 12 are flow charts, respectively, describing the computer software programs used for ferning data acquisition, and ferning index calculation.

In accordance with the present invention, the fertility monitor system of the present inventions include means for identifying if a sample slide has already been used and inserted into the monitor for testing. In a preferred embodiment, each glass slide for carrying the saliva sample is marked with a different barcode; and the monitor includes means to read and decode the barcode and store the data corresponding to the barcode. When a glass slide is inserted into the monitor, its barcode is read by the monitor and compared with the barcode data stored in the computer. If the same barcode data is not found in the computer storage, the monitor allows to start the ferning test. If, however, the same barcode is found in the computer storage, the monitor will provide a warning signal, such as a sound alarm or a flashing light indicator, and will not proceed to ferning testing. Advantageous, this will ensure that each glass slide is used only once and is not contaminated by any prior saliva samples.

As will be apparent to those skilled in the art, numerous modifications to the present invention may be made within the scope of the present invention, which is not intended to be limited except in accordance with the following claims.

We claim:

1. A method for determining ferning in a female, comprising:
   a. providing a sample obtained from a fluid from the female;
   b. irradiating the sample with laser light to generate a scattered light pattern from the sample; and
   c. analyzing the scattered light pattern to determine ferning in the female.

2. The method of claim 1 further comprising the step of excluding specularly reflected laser light from the scattered light pattern.

3. The method of claim 1 wherein the scattered light pattern is a diffraction pattern.

4. The method of claim 3, wherein the analyzing step comprises analyzing a spatial intensity profile of the diffraction pattern.

5. The method of claim 3, further comprising repeating the irradiating step at least once to obtain a plurality of diffraction patterns.

6. The method of claim 5, wherein the analyzing step comprises analyzing a spatial intensity profile of each of the plurality of diffraction patterns.

7. The method of claim 1 further comprising the step of correlating the degree of ferning with an ovulation status of the female.

8. The method of claim 7, wherein the correlating step further comprises determining a fertility cycle of the female.

9. The method of claim 1 further comprising the step of drying the sample prior to the irradiating step.

10. An ovulation monitoring apparatus for determining fernig in a female, comprising:
   a surface member adapted for supporting a sample obtained from a fluid from the female;
   a laser source configured to irradiate the sample with laser light sufficient to generate a scattered light pattern from the sample; and a detector positioned to obtain the scattered light pattern and a processor for evaluating the scattered light pattern to determine ferning in the female.

11. The ovulation monitoring apparatus of claim 10, wherein the detector measures an intensity profile and the processor analyzes the intensity profile of the scattered light pattern.

12. The ovulation monitoring apparatus of claim 11, wherein the scattered light pattern is a diffraction pattern and wherein the processor comprises computer software to compute at least one of a number of symmetrical peaks, an amplitude of symmetrical peaks, or an area under a plot of the intensity profile.

13. The ovulation monitoring apparatus of claim 10, further comprising a beam blocking element positioned between the sample and the detector to exclude specularly reflected laser light from the scattered light pattern.

14. The ovulation monitoring apparatus of claim 10, wherein the processor correlates measured ferning to the female's ovulation status.

* * * * *

UNITED STATES PATENT AND TRADEMARK OFFICE
CERTIFICATE OF CORRECTION

PATENT NO. : 6,159,159

DATED : December 12, 2000

INVENTOR(S) : Joseph M. CANTER; Yongwu YANG; Wanglong ZHOU; Victor S. SAPIRSTEIN; Melvin P. EHRLICH; James S. HARRISON; Eugene KATSMAN; Omanand KOUL; Michael Y. LU; Michael A. GREENWALD It is certified that errors appear in the above-identified patent and that said Letters Patent is hereby corrected as shown below:

1. The inventorship should be changed by deleting Messrs. Zhou, Sapirstein, Ehrlich, Harrison, Koul, Lu, and Greenwald and should read as follows:

Yongwu YANG; Joseph M. CANTER; Eugene KATSMAN.

2. Column 6, line 62, replace "fernig" with --ferning--.

Signed and Sealed this

First Day of May, 2001

*Attest:*

NICHOLAS P. GODICI

*Attesting Officer*     *Acting Director of the United States Patent and Trademark Office*